United States Patent [19]

Steiger et al.

[11] Patent Number: 5,662,827

[45] Date of Patent: Sep. 2, 1997

[54] DIQUATERNARY COMPOUNDS USEFUL AS BLEACH ACTIVATORS, AND COMPOSITIONS CONTAINING THEM

[75] Inventors: Philip H. Steiger, Powell, Ohio; Shaun F. Clancy, Westport, Conn.; Owen Portwood, Columbus, Ohio

[73] Assignee: Witco Corporation, Greenwich, Conn.

[21] Appl. No.: 393,063

[22] Filed: Feb. 23, 1995

Related U.S. Application Data

[63] Continuation-in-part of Ser. No. 192,455, Feb. 7, 1994, Pat. No. 5,399,746.

[51] Int. Cl.$^6$ .............................. C09K 3/00; C01B 15/10; C11D 3/39; C07C 67/02
[52] U.S. Cl. ................... 252/186.38; 510/312; 560/251; 554/104
[58] Field of Search ............... 252/186.38, 186.39; 510/312; 560/251; 554/104

[56] References Cited

U.S. PATENT DOCUMENTS

| | | | |
|---|---|---|---|
| 2,941,004 | 6/1960 | Pinson, Jr. et al. | 564/87 |
| 3,371,116 | 2/1968 | Nordgren et al. | 564/289 |
| 3,959,461 | 5/1976 | Bailey et al. | 424/70.28 |
| 4,006,092 | 2/1977 | Jones | 510/513 |
| 4,283,301 | 8/1981 | Diehl | 510/312 |
| 4,412,934 | 11/1983 | Chung et al. | 252/186.38 |
| 4,675,131 | 6/1987 | Walraevens et al. | 560/252 |
| 4,681,592 | 7/1987 | Hardy et al. | 8/111 |
| 4,818,426 | 4/1989 | Humphreys et al. | 510/375 |
| 4,933,103 | 6/1990 | Aoyagi et al. | 252/186.38 |
| 5,047,577 | 9/1991 | Smith et al. | 560/253 |
| 5,220,051 | 6/1993 | Sotoya et al. | 560/142 |
| 5,334,761 | 8/1994 | Gebeyehu et al. | 564/197 |
| 5,399,746 | 3/1995 | Steiger et al. | 560/251 |
| 5,422,028 | 6/1995 | Oakes et al. | 510/310 |

FOREIGN PATENT DOCUMENTS

| | | |
|---|---|---|
| 95/01164 | 2/1995 | European Pat. Off. . |
| 2574400 | 6/1986 | France . |
| 836988 | 6/1960 | United Kingdom . |
| 864798 | 4/1961 | United Kingdom . |
| 1147871 | 4/1969 | United Kingdom . |
| 1382594 | 2/1975 | United Kingdom . |

*Primary Examiner*—Joseph D. Anthony
*Attorney, Agent, or Firm*—Scully, Scott, Murphy & Presser

[57] ABSTRACT

Disclosed are bleaching compositions comprising diquaternary ammonium esters which are useful as bleach activators with a peroxygen compound to yield peroxide in solution.

18 Claims, No Drawings

DIQUATERNARY COMPOUNDS USEFUL AS BLEACH ACTIVATORS, AND COMPOSITIONS CONTAINING THEM

This application is a continuation-in-part of U.S. Ser. No. 08/192,455 filed Feb. 7, 1994, now U.S. Pat. No. 5,399,746.

BACKGROUND OF THE INVENTION

The present invention relates to bleaching compositions useful particularly in the bleaching of fabrics, and also in the treatment of paper pulp and in hard surface cleaning.

While it has been known for some time that compounds which yield hydrogen peroxide in water are effective bleaches, it is also known that the bleaching activity suffers substantially if the temperature of the bleaching solution is under 60° C. The loss of bleaching activity becomes increasingly pronounced as the temperature decreases. It has thus been proposed to use bleaching compositions which are a combination of one or more compounds which yield peroxide in solution, in combination with another compound, known as a "bleach activator", which in solution with the peroxide has the effect of promoting effective bleaching action even at temperatures below the temperature at which the peroxide compound, per se, would suffer loss of activity.

Certain ester compounds have been proposed as such bleach activators. For instance, U.K. Patent No. 864,798 and U.K. Patent No. 836,988, as well as U.K. Patent No. 1,147,871 and U.K. Patent No. 1,382,594, disclose bleaching compositions comprising an inorganic persalt and certain organic carboxylic acid esters. Other esters and their use in association with compounds which generate peroxide in aqueous solution are disclosed in U.S. Pat. No. 4,283,301 and U.S. Pat. No. 4,412,934. The aforementioned U.S. Pat. No. 4,283,301 also discloses certain alpha-omega-alkyldiesters.

Previous attempts to incorporate a quaternary nitrogen moiety into a bleach activator are described in the aforementioned U.K. Patent No. 1,382,594 and U.S. Pat. No. 5,047,577, both of which disclose certain monoesters said to be useful as bleach activators, and U.S. Pat. No. 4,675,131, which discloses a quaternary ammonium compound substituted by three ester groups.

While no particular theory is to be considered to limit the scope of this application, the performance observed in the art is consistent with the formation in solution of a persalt, characterized by the radical —C(O)OOH, formed by a reaction of the peroxide which is formed in solution with the ester group or groups which are present. Thus, some of the aforementioned patents describe the corresponding peracids believed to be formed, while other such peracids are disclosed in U.S. Pat. No. 4,681,592.

SUMMARY OF THE INVENTION

The present invention comprises, in various aspects thereof, bleaching compositions comprising bleach activators, and the use thereof to bleach substrates such as textiles, characterized by the improved properties described in greater detail below. Those improved properties include improved bleaching performance, the ability to exhibit satisfactory bleaching at lower temperatures, ease of handling, stability in formulation, and cost-effectiveness both in the relative inexpensiveness of the synthesis of the bleach activator and in the ability to obtain satisfactory bleaching performance with relatively smaller amounts of the bleach activator.

These and other advantages described herein are realized with compounds of the formulas (1), (2), or (3):

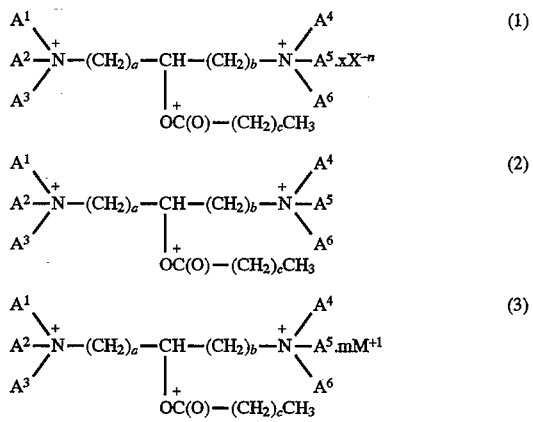

wherein $A^1$, $A^2$, $A^3$, $A^4$, $A^5$ and $A^6$ are the same or different, and each represents alkyl or alkoxyalkyl containing up to 6 carbon atoms, or one or two of $A^1$ and $A^4$ is benzyl, provided that in formula (1), one of $A^1$ and $A^4$ is optionally $-(CH_2)_{1-4}CO_2^-$ or $-(CH_2)_{1-4}SO_3^-$; in formula (2), two of $A^1$, $A^2$, $A^4$, and $A^5$ are selected from the group consisting of $-(CH_2)_{1-4}CO_2^-$ and $-(CH_2)_{1-4}SO_3^-$; and in formula (3) three or four of $A^1$, $A^2$, $A^3$, $A^4$, $A^5$, and $A^6$ are selected from the group consisting of $-(CH_2)_{1-4}CO_2^-$ and $-(CH_2)_{1-4}SO_3^-$;

a is 1 to 4;

b is 1 to 4;

c is 0 to 8;

n is 1 or 2; and

X is an anion preferably selected from the group consisting of chloride, bromide, iodide, methylsulfate, methylcarbonate, ethylsulfate, tosylate, mesylate and hydroxide.

Another aspect of the present invention comprises bleaching compositions which comprise a compound in accordance with formula (1), (2), or (3) above and a peroxygen bleaching component capable of yielding hydrogen peroxide in aqueous solution, the two being present in amounts relative to each other effective to form a solution having activity as a bleach.

DETAILED DESCRIPTION OF THE INVENTION

In formulas (1), (2), or (3) depicted above, $A^1$, $A^2$, $A^3$, $A^4$, $A^5$ and $A^6$ can be straight or branched alkyl containing 1 to 6 carbon atoms, and more preferably methyl or ethyl. These substituents can also be alkoxyalkyl, containing 2 to 6 carbon atoms, such as ethoxymethyl or ethoxyethyl. Straight, that is, unbranched, alkyl groups are preferred. Preferably, $A^1$, $A^2$, $A^3$, $A^4$, $A^5$ and $A^6$ are identical to each other.

Also, from 1 to 4 of $A^1$, $A^2$, $A^3$, $A^4$, $A^5$, and $A^6$ can be an anionic moiety, namely, $-(CH_2)_{1-4}CO_2^-$ or $-(CH_2)_{1-4}SO_3^-$. When such moieties are present, the amount of anion $X^{-1}$ or cation $M^{+1}$ must be adjusted so that the overall ionic charge of the molecule is zero, i.e., ionically (electrically) neutral. Of course, when exactly two of the anionic moieties are present, no balancing anion or cation is needed.

In formulas (1), (2), and (3), a is 1 to 4 and is preferably 1; b is 1 to 4 and is preferably 1; and c is 0 to 8 and is preferably 0–1 or 6–8.

The cation $M^{+1}$ is any cation that permits the compound of formula (3) to be water-soluble and not deleterious to the bleaching components, detergents, and substrates (clothing) with which it is used. Preferred cations are sodium, potassium, and ammonium. Most preferred is sodium.

The anion $X^{-1}$ is any anion that permits the compound of formula (1) to be water-soluble, and not deleterious to the bleaching components, detergents, and substrates (clothing) with which it is used. Preferred anions are selected from chloride, bromide, iodide, methylsulfate, methylcarbonate, ethylsulfate, and hydroxide. $X^{-1}$ is preferably chloride or methylsulfate.

Compounds of formulas (1), (2), and (3) having the foregoing definitions can readily be prepared from the corresponding (α-ω)-diaminoalkanol, such as 1,3 of this invention is described in greater detail in the examples below.

Alternatively, compounds of formulas (1), (2), and (3) can readily be prepared from the corresponding (α-ω)-diaminoalkanol by esterification with the corresponding acid $CH_3(CH_2)_cC(O)OH$ under esterifying conditions.

Compounds wherein c is 0 or 1 can be prepared by reaction of the corresponding (α-ω)-diaminoalkanol with the appropriate anhydride, e.g. acetic anhydride or propionic anhydride.

The anionic moieties $—(CH_2)_{1-4}CO_2^-$ and $—(CH_2)_{1-4}SO_3^-$ mentioned hereinabove can be attached employing known techniques, involving e.g. reaction of the ester with (Hal)—$(CH_2)_{1-4}CO_2H$ or (Hal)—$(CH_2)_{1-4}SO_3H$ wherein (Hal) is as defined herein. For instance, chloroacetic acid is one preferred reagent for this purpose.

The bleaching compositions of the present invention comprise a bleach activator component, comprising one or more compounds of the foregoing formulas (1), (2), or (3) in combination with a peroxygen bleaching component, by which is meant one or more compounds capable of yielding hydrogen peroxide in aqueous solution. Such compounds include inorganic peroxygen compounds, which are generally preferred, and organic adducts of hydrogen peroxide. Examples of preferred peroxy compounds include urea peroxide, alkali metal perborates, percarbonates, perphosphates, more particularly where the alkali metal is sodium. Particular preferred examples are sodium perborate (monohydrate or tetrahydrate), sodium percarbonate formulas (1), (2), or (3) in combination with a peroxygen bleaching component, by which is meant one or more compounds capable of yielding hydrogen peroxide in aqueous solution. Such compounds include inorganic peroxygen compounds, which are generally preferred, and organic adducts of hydrogen peroxide. Examples of preferred peroxy compounds include urea peroxide, alkali metal perborates, percarbonates, perphosphates, more particularly where the alkali metal is sodium. Particular preferred examples are sodium perborate (monohydrate or tetrahydrate), sodium percarbonate (sodium carbonate peroxyhydrate), sodium pyrophosphate peroxyhydrate, urea peroxyhydrate, and sodium peroxide. The most preferred peroxygen compounds are the monohydrate and tetrahydrate of sodium perborate and sodium percarbonate.

To form the bleaching compositions, the compound or compounds of formula (1), (2), or (3) and the peroxygen bleaching component should be mixed together in solid form intimately in relative amounts with respect to each other such that upon addition of the resulting product to an aqueous solution, hydrogen peroxide forms and reacts with the ester group on the bleach activator. Optionally the two components can be milled together to form a finely blended powder. The ratio of bleach to activator can be adjusted so that the molar ratio of peroxide generated in solution to activator is 2:1, 3:1 or higher, even 5:1 or higher. It is one noteworthy aspect of the present invention that effective bleaching at low temperatures is provided even when the mole ratio of peroxide generated in solution to the bleach activator is below about 1.5:1 or even about 1:1 or less. In this way, the operator will realize effectiveness and efficiency in that less of the bleach activator needs to be used to achieve a particular desired degree of bleaching in the solution.

In laundry washing and bleaching applications, the amount of the bleach composition to use may vary typically between about 500 to 3,000 ppm in the wash water, and preferably about 1,000 to 1,500 ppm.

Bleaching compositions prepared in accordance with the foregoing description exhibit advantageous bleaching activity, at high wash water temperatures on the order of 60° C. or above and notably at lower washing temperatures ranging from 10° C. to 60° C. In addition, the bleaching performance per unit of material is unexpectedly enhanced, perhaps because of the diquaternary nature of the molecule. As an additional advantage, the peracid $CH_3(CH_2)_cC(O)OOH$, which is believed to be formed, appears able to achieve close penetration to the surface of the material being bleached, thereby enhancing the effectiveness.

The bleach compositions according to the present invention maybe formulated into bleach/detergent compositions by adding one or more surfactants to impart detergency activity to the composition. Preferred detergent surfactants include nonionic, anionic, and zwitterionic surfactants such as those described in U.S. Pat. No. 4,006,092 from Col. 12, line 52 to Col. 19, line 11 the disclosure of which is hereby incorporated herein by reference. Such surfactants should represent about 1% to about 60%, and preferably about 5% to about 40% by weight of the concentrated bleaching composition. Despite the belief stated in some publications that conventional anionic surfactants may tend to interact unfavorably with the bleach activators, the bleach activators of the present invention have been found not to suffer impaired performance when in solution with anionic surfactants. Conventional cationic surfactants may be used in minor amounts alone or in combination with the above nonionic, anionic, or zwitterionic surfactants. Preferred surfactants for use in combination with the bleach composition of the present invention are polyethyleneoxide condensates of alkyl phenols, the condensation products of aliphatic alcohols with ethylene oxide, and the amide oxide and sulfoxide surfactants, or mixtures thereof. Especially preferred are the ethylene oxide condensates of alkyl phenols or aliphatic alcohols which are capped at the terminal hydroxyl group to prevent possible ester interchange reactions with the activator compounds, suitable capping groups include short chain ($C_{1-4}$) alkyl ethers, acetate, benzyl ether, and the like.

In order to promote optimum bleaching of substrates, particularly fabrics (by which is meant woven and non-woven fabrics of natural fibers, synthetic fibers, and blends thereof), it is preferred that the bleaching compositions of the present invention also contain buffering agents effective to adjust the pH of the composition in aqueous solution to a range of about 7 to about 12, and preferably about 8.5 to about 10.5. Suitable buffering agents include orthophosphates, water-soluble condensed phosphates such as tripolyphosphates, and pyrophosphates, carbonates, bicarbonates, and silicates. More preferred examples of buffering agents include sodium bicarbonate, sodium carbonate, disodium hydrogen phosphate, sodium dihydrogen phosphate and sodium tetrapyrophosphate. Other buffering agents meeting the criteria described herein will be readily ascertainable by those of ordinary skill in this art.

Bleaching and cleansing compositions incorporating the bleach activators of the present invention can also be formulated into hard surface cleaning products, cleaners for use in automatic dishwashers, and soft or solid stick-type products used for applying a bleaching/cleaning composition to selected soiled spots of a surface.

The invention will be described further in the following examples.

EXAMPLE 1

1.1 gr of 1,3-bis-dimethylamino-2-propanol was dissolved in 50 ml of methylene chloride. Octanoyl chloride was added in the amount of 1.1 molar equivalents (1.35 gr). The mixture became cloudy and slightly warm. It was placed on a heated stirring plate and refluxed for 90 minutes. The product was then worked up by adding a solution of 1 gram $NaHCO_3$ in about 50 ml of water, stirring for 10 minutes and extracting three times with methylene chloride. The solution of product in methylene chloride was dried over sodium sulfate and filtered into a flask. The filtered product was dissolved in 50 ml of toluene to form a solution which was then rotoevaporated at 70° C. to yield 2.06 gr of a liquid product.

The liquid product thus recovered was dissolved in about 50 ml of acetonitrile, to which was then added 2.05 molar equivalents (1.94 gr=1.45 ml) of dimethyl sulfate. This mixture was stirred and refluxed for 3 hours. The acetonitrile was then removed by rotoevaporation to yield 4.39 gr of a solid product which was taken up in 50 ml of toluene and reevaporated to remove moisture. The resulting product, a solid, was tested and found to function as a bleach activator.

EXAMPLE 2

1.0 mole of 1,3-bis-dimethylamino-2-propanol was added to 1.0 mole of a 60:40 (wt. %) mixture of octanoic and decanoic acids and the mixture heated to 150° C. under reduced pressure and a nitrogen sparge to remove water of esterification. The reaction was continued until the acid value of the mixture was less than 2. Since some amine was carried away by the water of esterification more amine was added during the reaction. The product ester-diamine was then transferred to a pressure reactor containing 250 ml acetonitrile. The reactor was closed and pressurized to 60 psi with methyl chloride. The reactor was heated to 60° C. and the reaction continued until the amine value was below 2. At that point the reactor was cooled, the methyl chloride removed, and the acetonitrile solution recovered. Acetonitrile was removed leaving 0.9 mole of product. The resulting product (a mixture of the 1,3-bis-trimethylammonium isopropyl esters of octanoic and decanoic acids) was tested and found to function as a bleach activator.

EXAMPLE 3

A comparative test was conducted to demonstrate the effectiveness of the bleach activators of the present invention. The "control" was a leading brand of detergent available nationally to household consumers. It contains neither bleach nor bleach activator. In each test the same amount of detergent was used. The bleach used was sodium perborate; when it was used, the amount used was 5 wt. % which is within the normal range of amounts of bleach in conventional clothes washing operations. The activator used was a mixture of the 1,3-bis-trimethylammonium isopropyl esters of octanoic and decanoic acids. When it was used, the amount used corresponded to a ratio of 3 moles of perborate per mole of the mixture of activators. The swatches were subjected to normal laundering in one of the indicated compositions and were then rinsed and dried. The whiteness was measured as a percent reflectance value; improvement in the whiteness of the bleached fabric swatches is shown as an increase in the percent reflectance. The following table shows the percent reflectance values that were measured:

| Stain | Control | Control+ perborate bleach | Control+ perborate bleach+ activator |
|---|---|---|---|
| Tea on cotton | 41% ± 2 | 51% ± 2 | 61% ± 2 |
| Blueberry on cotton | 55% ± 1 | 63% ± 1 | 67% ± 1 |
| Immedial black* on cotton | 4% ± 1 | 5% ± 1 | 10% ± 1 |
| Tea on cotton/polyester | 6% ± 1 | 11% ± 1 | 23% ± 1 |

*Immedial black is used in order to represent an ink type of stain and is very difficult to remove.

In all of the instances cited, the presence of the activator improved the bleaching effect of the composition, compared to the perborate alone.

What is claimed is:

1. A bleaching composition comprising
   (a) a peroxygen bleaching component which comprises one or more compounds capable of yielding hydrogen peroxide in aqueous solution; and
   (b) one or more compounds of the formula (1), (2) or (3)

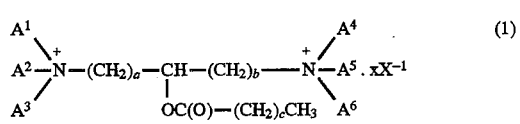

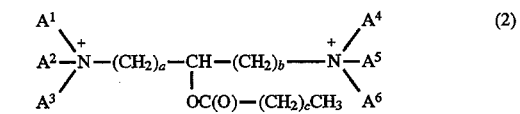

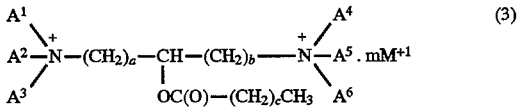

wherein $A^1$, $A^2$, $A^3$, $A^4$, $A^5$ and $A^6$ are the same or different and are selected from the group consisting of alkyl containing up to 6 carbon atoms, and alkoxyalkyl containing up to 6 carbon atoms; provided that in formula (1), one of $A^1$ and $A^4$ is optionally $—(CH_2)_{1-4}CO_2^-$ or $—(CH_2)_{1-4}SO_3^-$; in formula (2), two of $A^1$, $A^2$, $A^4$, and $A^5$ are selected from the group consisting of $—(CH_2)_{1-4}CO_2^-$ and $—(CH_2)_{1-4}SO_3^-$; and in formula (3) three or four of $A^1$, $A^2$, $A^3$, $A^4$, $A^5$, and $A^6$ are selected from the group consisting of $—(CH_2)_{1-4}CO_2^-$ and $—(CH_2)_{1-4}SO_3^-$;

$X^{-1}$ is an anion;

$M^{+1}$ is a cation;

a is 1 to 4;

b is 1 to 4;

c is 5 to 8;

x is 1 or 2 and is selected so that the compound of formula (1) is ionically neutral; and m is 1 or 2 and is selected so that the compound of formula (3) is ionically neutral.

2. A bleaching composition according to claim 1 wherein the peroxygen bleaching component is selected from the group consisting of urea peroxide, alkali metal perborates, alkali metal percarbonates, alkali metal perphosphates, and mixtures thereof.

3. A bleaching composition according to claim 1 wherein $X^{-1}$ is an anion selected from the group consisting of chloride, bromide, iodide, methylsulfate, methylcarbonate, ethylsulfate and hydroxide.

4. A bleaching composition according to claim 1 wherein $M^{+1}$ is a cation selected from the group consisting of sodium, potassium, and ammonium.

5. A bleaching composition according to claim 1 wherein a is 1.

6. A bleaching composition according to claim 1 wherein b is 1.

7. A bleaching composition according to claim 1 wherein c is 5–8.

8. A bleaching composition according to claim 1 wherein $X^{-1}$ is methylsulfate or chloride.

9. A composition according to claim 1 wherein the mole ratio of peroxide generated in solution to component (b) is less than 1.5:1.

10. A method of bleaching fabric comprising immersing the fabric in an aqueous solution of a bleaching composition according to claim 1.

11. A composition according to claim 1 wherein said peroxygen bleaching component and said one or more compounds of formula (1), (2) or (3) are present in relative amounts with respect to each other such that upon addition of said composition to an aqueous solution hydrogen peroxide forms and reacts with the ester group on said compound of formula (1), (2), or (3).

12. A bleaching composition according to claim 1 where the peroxygen bleaching component is selected from the group consisting of sodium perborate monohydrate, sodium perborate tetrahydrate, sodium carbonate peroxyhydrate, sodium pyrophosphate peroxyhydrate, urea peroxyhydrate, sodium peroxide, and mixtures thereof.

13. A bleaching composition according to claim 12 wherein the peroxygen bleaching component is sodium perborate monohydrate, sodium perborate tetrahydrate, or a mixture thereof.

14. A bleaching composition according to claim 1 wherein $A^1, A^2, A^3, A^4, A^5$ and $A^6$ are the same or different and each is straight or branched alkyl containing 1 to 6 carbon atoms.

15. A bleaching composition according to claim 14 wherein $A^1, A^2, A^3, A^4, A^5$ and $A^6$ are identical to each other.

16. A bleaching composition according to claim 1 wherein $A^1, A^2, A^3, A^4, A^5$ and $A^6$ are identical to each other and are alkyl containing 1 to 6 carbon atoms, a is 1, b is 1, and c is 6–8.

17. A bleaching composition according to claim 16 wherein $X^{-1}$ is methylsulfate or chloride.

18. A method of bleaching fabric comprising immersing the fabric in an aqueous solution of a bleaching composition according to claim 16.

* * * * *

UNITED STATES PATENT AND TRADEMARK OFFICE
CERTIFICATE OF CORRECTION

PATENT NO. : 5,662,827
DATED : September 2, 1997
INVENTOR(S) : Philip H. Steiger, et al.

It is certified that error appears in the above-indentified patent and that said Letters Patent is hereby corrected as shown below:

Column 2, lines 5, 10 & 15: delete " + "

Signed and Sealed this

Seventeenth Day of November, 1998

Attest:

BRUCE LEHMAN

Attesting Officer

Commissioner of Patents and Trademarks